US012591969B2

(12) United States Patent
Arita et al.

(10) Patent No.: US 12,591,969 B2
(45) Date of Patent: Mar. 31, 2026

(54) MEDICAL INFORMATION PROCESSING APPARATUS, METHOD AND NON-TRANSITORY COMPUTER-READABLE STORAGE MEDIUM TO ACQUIRE BIOMETRIC DATA REGARDING SKIN IMAGE AND TO CONTINUOUSLY MONITOR INTERNAL BODY COMPONENT WITHOUT USING SPECIAL EQUIPMENT

(71) Applicant: CANON MEDICAL SYSTEMS CORPORATION, Otawara (JP)

(72) Inventors: Kosuke Arita, Nasushiobara (JP); Longxun Piao, Nasushiobara (JP); Sho Sasaki, Utsunomiya (JP); Yudai Yamazaki, Nasushiobara (JP); Yuka Shimomura, Nasushiobara (JP); Asateru Kimura, Otawara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 358 days.

(21) Appl. No.: 18/329,851

(22) Filed: Jun. 6, 2023

(65) Prior Publication Data

US 2023/0410302 A1    Dec. 21, 2023

(30) Foreign Application Priority Data

Jun. 10, 2022    (JP) ................................ 2022-094493

(51) Int. Cl.
*G06T 7/00*        (2017.01)
*G16H 10/60*      (2018.01)
(Continued)

(52) U.S. Cl.
CPC ........... *G06T 7/0012* (2013.01); *G16H 10/60* (2018.01); *G16H 50/20* (2018.01);
(Continued)

(58) Field of Classification Search
None
See application file for complete search history.

(56) References Cited

U.S. PATENT DOCUMENTS

| | | | | |
|---|---|---|---|---|
| 8,824,746 B2 * | 9/2014 | Abe | ..................... | G06V 10/993 |
| | | | | 382/128 |
| 2009/0196475 A1 * | 8/2009 | Demirli | ................ | G06V 40/162 |
| | | | | 382/128 |

(Continued)

FOREIGN PATENT DOCUMENTS

| | | |
|---|---|---|
| JP | 2017-512577 A | 5/2017 |
| JP | 2021-62080 A | 4/2021 |
| WO | WO 2015/153362 A1 | 10/2015 |

OTHER PUBLICATIONS

Jolivot et al., "Skin Parameter Map Retrieval from a Dedicated Multispectral Imaging System Applied to Dermatology/ Cosmetology" Hindawi Publishing Corporation IJBI, vol. 2013, Article ID 978289, Sep. 18, 2013, 17 pages.

*Primary Examiner* — Haris Sabah
(74) *Attorney, Agent, or Firm* — Oblon, McClelland, Maier & Neustadt, L.L.P.

(57) ABSTRACT

A medical information processing apparatus of an embodiment includes processing circuitry. The processing circuitry acquires biometric data regarding a subject. The processing circuitry identifies reference data regarding a first feature amount on the basis of the biometric data. The processing circuitry acquires a second feature amount by inputting the first feature amount included in the biometric data into a model capable of mutually converting the first feature amount and the second feature amount. The processing circuitry derives pseudo-feature data regarding the first feature amount simulated by inputting the second feature amount into the model. The processing circuitry determines (Continued)

reliability scores with respect to the biometric data on the basis of the reference data and the pseudo-feature data.

12 Claims, 10 Drawing Sheets

(51) Int. Cl.
    *G16H 50/20*          (2018.01)
    *H04N 1/407*         (2006.01)
    *H04N 1/60*          (2006.01)

(52) U.S. Cl.
    CPC .... *G06T 2207/30004* (2013.01); *H04N 1/407* (2013.01); *H04N 1/6005* (2013.01)

(56)              References Cited

U.S. PATENT DOCUMENTS

| | | | | |
|---|---|---|---|---|
| 2016/0314585 | A1* | 10/2016 | Thomas | G06V 40/10 |
| 2019/0014431 | A1* | 1/2019 | Lee | H04S 7/303 |
| 2019/0392189 | A1* | 12/2019 | Kumar | G06V 40/1312 |

* cited by examiner

MEDICAL INFORMATION PROCESSING APPARATUS, METHOD AND NON-TRANSITORY COMPUTER-READABLE STORAGE MEDIUM TO ACQUIRE BIOMETRIC DATA REGARDING SKIN IMAGE AND TO CONTINUOUSLY MONITOR INTERNAL BODY COMPONENT WITHOUT USING SPECIAL EQUIPMENT

CROSS-REFERENCE TO RELATED APPLICATION

The present application claims priority based on Japanese Patent Application No. 2022-094493 filed Jun. 10, 2022, the content of which is incorporated herein by reference.

FIELD OF THE INVENTION

Background of the Invention

Embodiments of the present invention relate to a medical information processing apparatus, a medical information processing method, and a storage medium.

Description of Related Art

Conventionally, internal body component amounts such as a hemoglobin concentration and a blood oxygen saturation have become important information for detecting the onset of diseases. A hemoglobin concentration can be a clue for diagnosis of diseases that cause blood flow-induced skin changes, such as heart failure accompanied by changes in blood flow and varicose veins in lower extremities accompanied by venous blood stasis. In order to detect the onset of such diseases at an early stage, it is necessary to continuously monitor internal body component amounts. In that case, a method capable of easily performing measurement in a hospital room or at home without using special equipment is desirable. As methods of measuring internal body component amounts without using special equipment, a method of searching for and determining the amount of an internal skin component that minimizes differences between luminance values and actual measurement values calculated by Monte Carlo modeling of light transport in multi-layered tissues (MCML) using an optical camera and a physical model, and a method of searching for the amount of an internal skin component using a genetic algorithm are known. However, since these methods use only calculated differences between luminance values and actual measurement values as criteria for determining a component amount, the same luminance value is obtained for a plurality of component amounts with different combinations and thus uniqueness of a solution is not satisfied, and internal body component amounts close to the actual physical condition of a subject such as a patient cannot be identified due to inconsistency in search ranges in some cases.

BRIEF DESCRIPTION OF THE DRAWINGS

FIG. 5 is a diagram showing a second derivation function.

DETAILED DESCRIPTION OF THE INVENTION

A medical information processing apparatus, a medical information processing method, and a storage medium according to embodiments will be described below with reference to the drawings.

A medical information processing apparatus of an embodiment includes processing circuitry. The processing circuitry acquires biometric data regarding a subject. The processing circuitry identifies reference data regarding a first feature amount on the basis of the biometric data. The processing circuitry acquires a second feature amount by inputting the first feature amount included in the biometric data into a model capable of mutually converting the first feature amount and the second feature amount. The processing circuitry derives pseudo-feature data regarding the first feature amount simulated by inputting the second feature amount into the model. The processing circuitry determines reliability scores with respect to the biometric data on the basis of the reference data and the pseudo-feature data.

Figure 1:
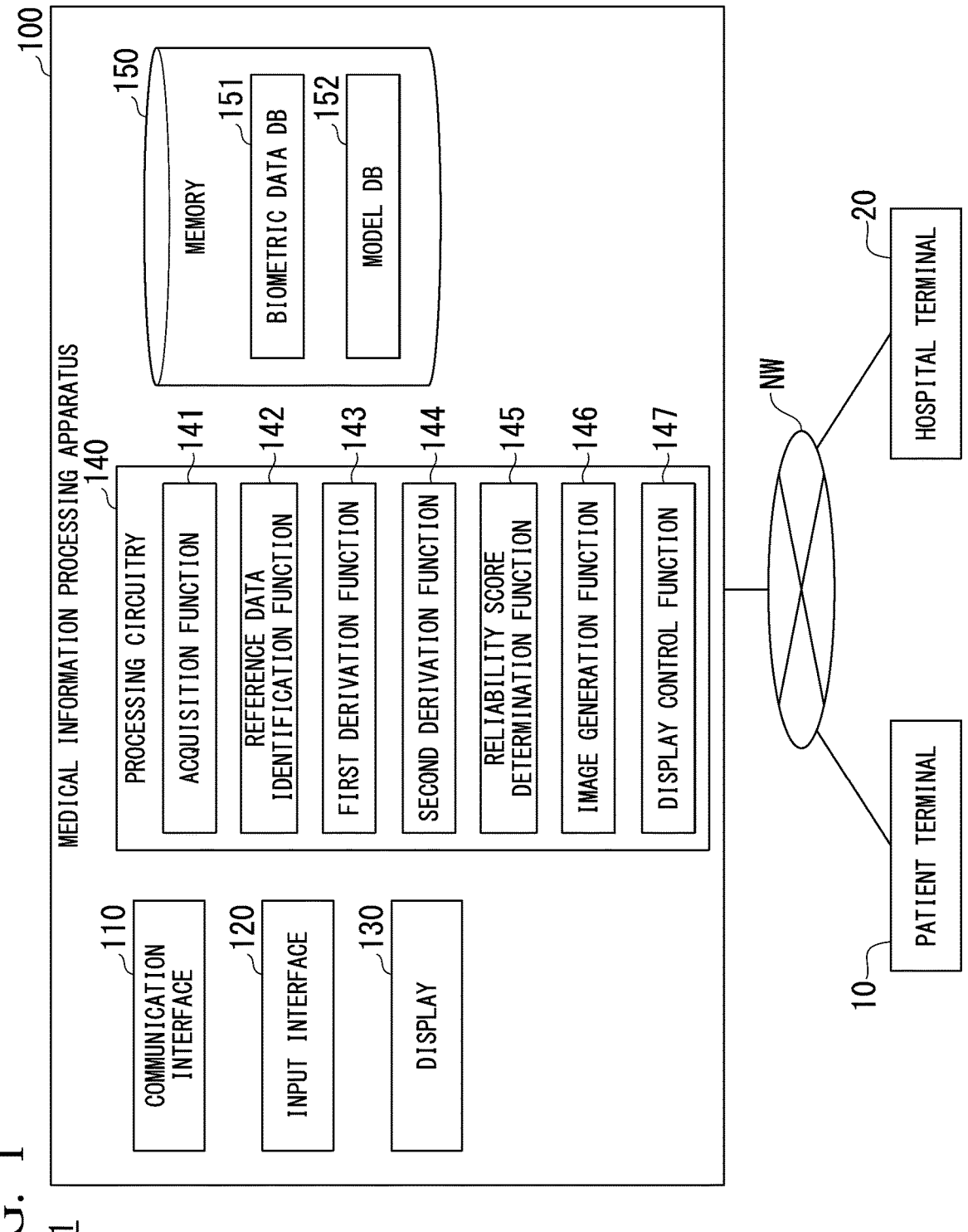
FIG. 1 is a diagram showing an example of a configuration of a medical information system including a medical information processing apparatus of an embodiment.

FIG. 1 is a diagram showing an example of a configuration of a medical information system 1 including a medical information processing apparatus according to an embodiment. The medical information system 1 includes, for example, a patient terminal 10, a hospital terminal 20, and a medical information processing apparatus 100. The patient terminal 10, the hospital terminal 20, and the medical information processing apparatus 100 are connected via a network NW such that they can communicate, for example. At least one of the patient terminal 10 and the hospital terminal 20 may be provided in the medical information system 1.

The network NW refers to a general information communication network using telecommunication technology. The network NW includes a wireless/wired local area network (LAN), a wide area network (WAN), an Internet network, a telephone communication network, an optical fiber communication network, a cable communication network, a satellite communication network, and the like.

The patient terminal 10 acquires biometric data regarding a patient (an example of a subject) and transmits the acquired biometric data to the medical information processing apparatus 100 via the network NW. Biometric data is, for example, data from which parameters of internal body components of a patient can be obtained. Biometric data includes, for example, patient skin images and information (e.g., absorbance) acquired by various sensors. Parameters of internal body components are, for example, internal body component amounts such as a hemoglobin concentration (hereinafter, Hb concentration) and a melanin concentration (hereinafter, Me concentration). In addition, the parameters of the internal body components may include an epidermal thickness, a dermal thickness, and the like of the skin of a patient. Further, the parameters of the internal body components may include oxygen saturation in blood, a blood sugar level, and the like.

The patient terminal 10 transmits biometric data in one or more phases. In addition, at the time of transmitting biometric data, the patient terminal 10 may transmit patient information (e.g., identification information for identifying a patient) and biometric data basic information (e.g., information on the type and acquisition date and time of biometric data). The patient terminal 10 is a device having a function of executing processing described above and is, for example, a smartphone, a tablet terminal, a camera device, or a wearable terminal.

The hospital terminal 20 acquires results of processing performed by the medical information processing apparatus 100 via the network NW and displays the acquired information to provide a patient's condition to a user such as a doctor. The hospital terminal 20 may be an installation type personal computer (PC), server, or the like, or a portable smartphone, tablet terminal, or the like.

The medical information processing apparatus 100 receives the biometric data transmitted from the patient terminal 10 and performs processing such as quantifying the reliability of internal body component amounts from the biometric data. Further, the medical information processing apparatus 100 displays processing results on a display thereof or transmits the processing results to the hospital terminal 20 via the network NW.

Here, the functional configuration of the medical information processing apparatus 100 will be described. The medical information processing apparatus 100 includes, for example, a communication interface 110, an input interface 120, a display 130, processing circuitry 140, and a memory 150.

The communication interface 110 includes, for example, a communication interface such as a network interface controller (NIC). The communication interface 110 communicates with external devices such as the patient terminal 10 and the hospital terminal 20 via the network NW, and outputs acquired information to the processing circuitry 140 and the like. Further, the communication interface 110 transmits information to an external device such as the hospital terminal 20 connected via the network NW under the control of the processing circuitry 140.

The input interface 120 receives various input operations from the user, converts the received input operations into electrical signals, and transmits the electrical signals to the processing circuitry 140. For example, when an input operation is performed by the user, the input interface 120 generates information according to the input operation. The input interface 120 transmits the generated information according to the input operation to the processing circuitry 140. The input interface 120 is realized by, for example, a mouse, a keyboard, a trackball, a switch, a button, a joystick, a touch panel, or the like. Further, the input interface 120 may be realized by, for example, a user interface that receives voice input such as a microphone. If the input interface 120 is a touch panel, the display 130 which will be described later may be formed integrally with the input interface 120.

The display 130 displays various types of information. For example, the display 130 displays an image generated by the processing circuitry 140, a graphical user interface (GUI) for receiving various input operations from the user, and the like. For example, the display 130 is a liquid crystal display (LCD), a cathode ray tube (CRT) display, an organic electroluminescence (EL) display, or the like.

The processing circuitry 140 includes, for example, an acquisition function 141, a reference data identification function 142, a first derivation function 143, a second derivation function 144, a reliability score determination function 145, an image generation function 146, and a display control function 147. The processing circuitry 140 realizes these functions by, for example, a hardware processor executing a program stored in a storage device (storage circuit).

The hardware processor is, for example, circuitry such as a central processing unit (CPU), a graphics processing unit (GPU), an application specific integrated circuit (ASIC) and a programmable logic device (for example, a simple programmable logic device (SPLD), a complex programmable logic device (CPLD), or a field programmable gate array (FPGA)).

The program may be directly incorporated into the circuit of the hardware processor instead of being stored in the storage device. In this case, the hardware processor realizes the functions by reading and executing the program incorporated into the circuit. The aforementioned program may be stored in a storage device in advance, or may be stored in a non-transitory storage medium such as a DVD or a CD-ROM and installed in the storage device from the non-transitory storage medium when the non-transitory storage medium is set in a drive device (not shown) of the medical information processing apparatus 100.

The hardware processor is not limited to being configured as a single circuit and may be configured as a single hardware processor by combining a plurality of independent circuits to realize each function. Further, a plurality of components may be integrated into one hardware processor to realize each function.

The memory 150 is realized by, for example, a semiconductor element such as a random access memory (RAM) and a flash memory, a hard disk, an optical disc, or the like. These non-transitory storage media may be realized by other storage devices such as a network attached storage (NAS) and external storage server devices connected via the network NW. Further, these non-transitory storage media may be realized by storage devices such as a read only memory (ROM) and a register. The memory 150 stores, for example, biometric data DB 151, a model DB 152, programs, and other various types of information.

The acquisition function 141 acquires biometric data transmitted from the patient terminal 10 via the communication interface 110. Further, the acquisition function 141 may store the acquired biometric data in the biometric data DB 151 in association with patient information, biometric data basic information, and the like. Further, the acquisition function 141 may acquire biometric data from the biometric data DB 151. The biometric data DB 151 may be acquired from an external device via the network NW.

In addition, the acquisition function 141 may acquire information that can be converted from the acquired biometric data in a predetermined manner using models stored in the model DB 152. The models stored in the model DB 152 are a physical model and a mathematical model that can mutually convert a first feature amount and a second feature amount by simulation or the like. The first feature amount is, for example, a feature amount derived from biometric data. The first feature amount is, for example, the luminance value and absorbance of an image. The second feature amount is a feature amount derived from the first feature amount. The second feature amount is, for example, a parameter of an internal body component. Hereinafter, acquiring the first feature amount simulated by inputting the second feature amount into a model may be referred to as "forward problem analysis" and acquiring the second feature amount simulated by inputting the first feature amount into a model may be referred to as "reverse problem analysis." Further, data regarding another feature amount simulated by inputting one of the first feature amount and the second feature amount into a model may be referred to as "pseudo-feature data."

Models stored in the biometric data DB 151 include, for example, a model that mutually converts the first feature amount and the second feature amount by a skin light reflection estimation method based on the Kubelka-Munk theory (hereinafter referred to as a "first model"), a model that mutually converts the first feature amount and the second feature amount by light scattering simulations in biological tissues using MCML (hereinafter referred to as a "second model"), a physical model that formulates absorption of light by a substance using the Lambert-Beer's law and mutually converts the first feature amount and the second feature amount (hereinafter referred to as a "third model"), and the like. The model DB 152 may be acquired from an external device via the network NW.

For example, the acquisition function 141 acquires a luminance value from a skin image included in the biometric data when the first model or the second model is used in subsequent processing (for example, processing of the first derivation function 143 and the second derivation function 144) and acquires an absorbance from sensor results included in the biometric data when the third model is used.

In addition, the acquisition function 141 may perform processing (preprocessing) such as smoothing filtering and edge extraction removal on the biometric data in order to remove information serving as noise (for example, information on palm prints, wrinkles, and hairs included in images) in deriving parameters of internal body components included in the biometric data. Furthermore, the acquisition function 141 may acquire data of a single time phase or may acquire data of a plurality of time phases in time series.

Figure 2:
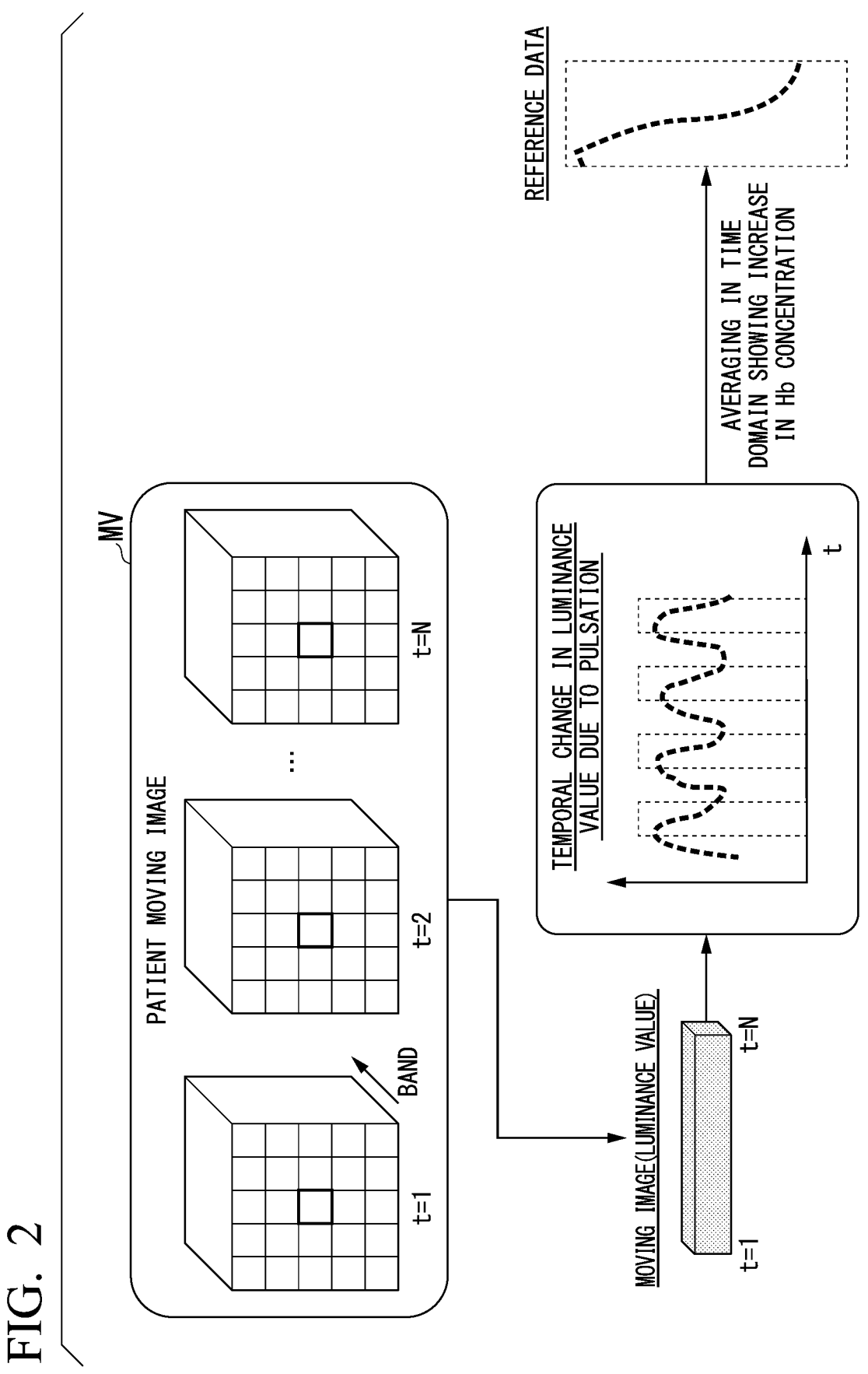
FIG. 2 is a diagram showing a reference data identification function.

The reference data identification function 142 identifies features (reference data) based on changes in parameters of internal body components. Reference data is, for example, an index value indicating a feature reflecting change in an internal body component amount to be identified. FIG. 2 is a diagram showing the reference data identification function 142. In the following, it is assumed that a patient moving image MV is used as biometric data, a luminance value is used as the first feature amount, and an Hb concentration is used as the second feature amount. The luminance value is, for example, at least one luminance value of RGB. As an example, the luminance value of R (red) is used in the following. The patient moving image MV is, for example, images of a plurality of time phases of the same region of the patient's skin captured at different times t (for example, skin images from which the color of blood in the skin can be extracted). The patient moving image MV may include band information.

The reference data identification function 142 identifies reference data regarding a luminance value from a skin image for each time phase included in the patient moving image MV. For example, the blood flow rate in the body also increases or decreases (blood flow changes) depending on the cycle of contraction and expansion of the heart due to pulsation. For example, during contraction, the blood flow rate increases (the hemoglobin concentration increases), and thus the absorbance of hemoglobin in the blood increases and the luminance value decreases. On the other hand, during expansion, the blood flow rate decreases (the hemoglobin concentration decreases), and thus the absorbance of hemoglobin decreases and the luminance value increases. Accordingly, the luminance values of pixels in the same place in an image region also repeatedly periodically increase and decrease as time elapses, as shown in FIG. 2. Therefore, the reference data identification function 142 identifies, as reference data, information (luminance value change portion) indicating change in a luminance value of a predetermined region in temporal changes in luminance values caused by pulsation. This reference data may be regarded as information indicating change in the Hb concentration in a predetermined region.

In the example of FIG. 2, the reference data identification function 142 extracts luminance values of a time domain indicating increase in the Hb concentration (a range from the maximum value (convex portion) to the minimum value (concave portion) of the waveform indicating increase/decrease in the luminance value) from the periodic changes in the luminance value. The reference data identification function 142 identifies reference data by averaging luminance values in a plurality of time domains indicating increase in the Hb concentration, as shown in FIG. 2. Accordingly, it is possible to curb luminance value variations in each time domain. The reference data identification function 142 may identify reference data by selecting one of a plurality of time domains indicating increase in the Hb concentration. Further, the reference data identification function 142 may identify, as reference data, luminance values in a time domain (a range from the minimum value to the maximum value of the luminance value) indicating decrease in the Hb concentration.

Figure 3:
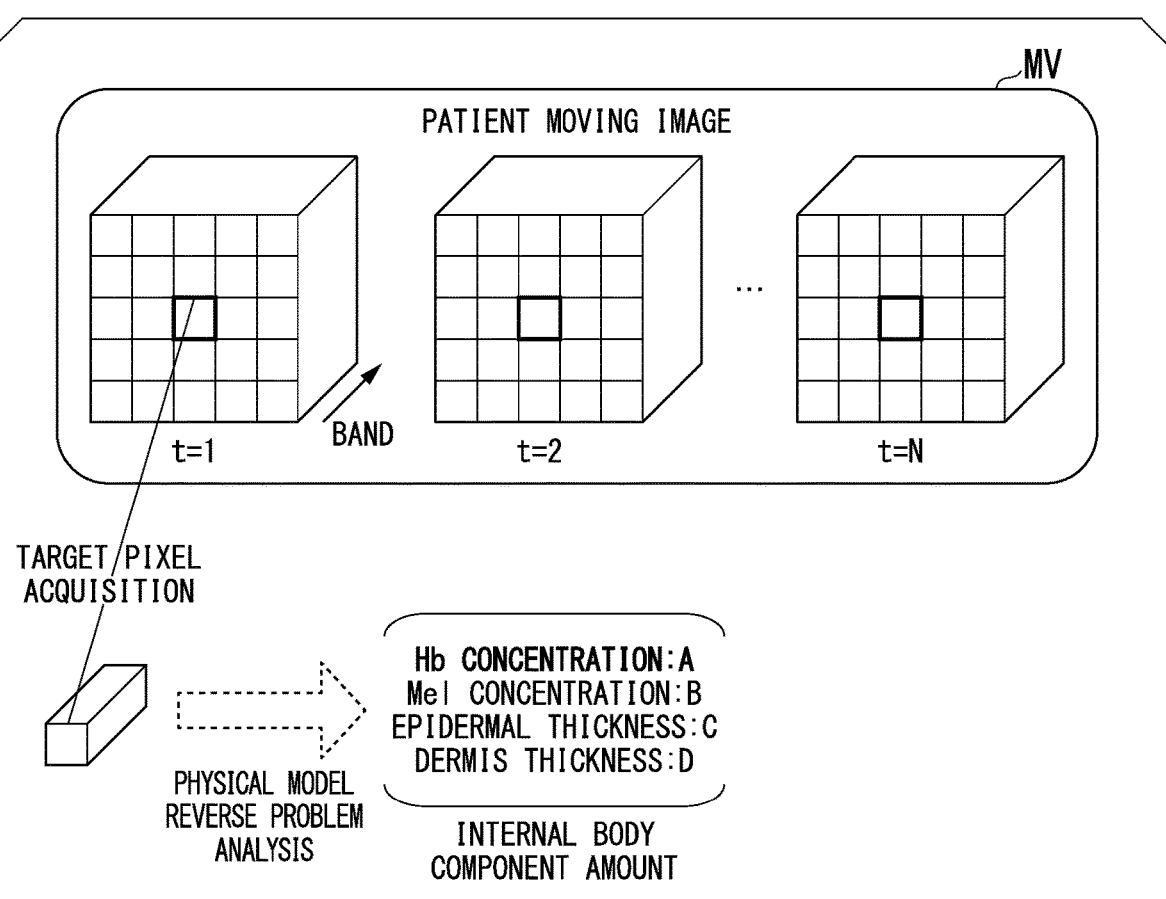
FIG. 3 is a diagram showing a first derivation function.

The first derivation function 143 inputs luminance values included in the biometric data into a model and derives internal body component amounts including the Hb concentration. FIG. 3 is a diagram showing the first derivation function 143. For example, the first derivation function 143 inputs luminance values of pixels in the same place as the place where reference data is acquired for each time phase from the patient moving image MV, which is biometric data, into a model stored in the model DB 151 (for example, a physical model such as the first model or the second model) to derive internal body component amounts according to problem analysis.

Figure 4:
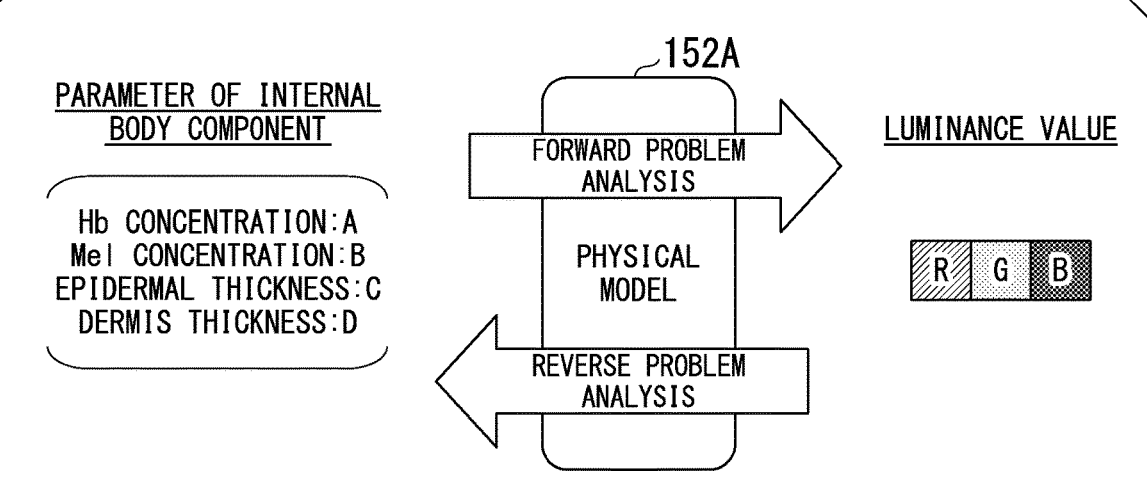
FIG. 4 is a diagram showing problem analysis using a model.

FIG. 4 is a diagram showing problem analysis using a model. For example, the model used in the first derivation function 143 and the second derivation function 144 (e.g., a physical model 152A) is a model that receives parameters (e.g., Hb concentration: A, Mel concentration: B, epidermal thickness: C, and dermis thickness: D) of internal body components as inputs and outputs luminance values (RGB values) according to forward problem analysis. In this case, the first derivation function 143 derives the internal body component parameters from the luminance values (RGB values) of pixels for each time phase according to reverse problem analysis using this physical model 152A.

Figure 5:
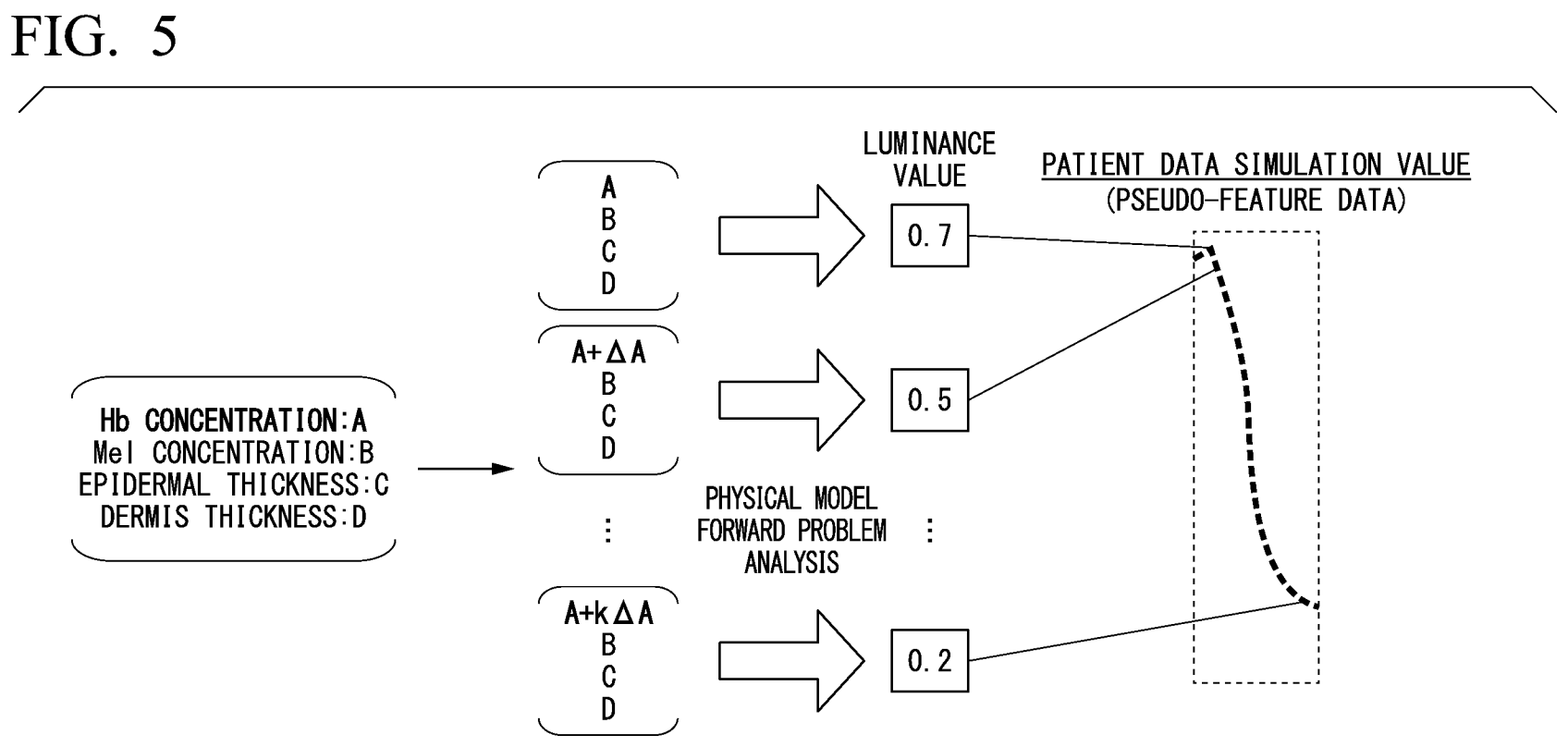

The second derivation function 144 receives the parameters of the internal body components derived by the first derivation function 143 as inputs and derives luminance value data (pseudo-feature data) simulated such that it can be compared with reference data. FIG. 5 is a diagram showing the second derivation function 144. The second derivation function 144 inputs the value of at least data (Hb concentration) corresponding to the reference data among the parameters (e.g., Hb concentration: A, Mel concentration: B, epidermal thickness: C, and dermis thickness: D) of the internal body components into the physical model 152A while changing the data by each predetermined amount, and derives values repeatedly obtained by forward problem analysis of the physical model 152A as pseudo-feature data (referred to as "patient simulation data" in FIG. 5) regarding the simulated first feature amount. The predetermined amount may be a fixed amount or may be variably set for each internal body component. Further, the number of times of changing by each predetermined amount (the number of repetitions) may be set on the basis of the elapsed time of the reference data to be compared, or may be a fixed number.

The second derivation function 144 may generate a set of internal body component amounts obtained by increasing the Hb concentration by each predetermined amount by the aforementioned number of times, input the generated set into the model, and derive luminance values for the set of internal body component amounts. Further, the second derivation function 144 may normalize a luminance value range (0 to 255) within a predetermined range (for example, the range of 0 to 1) as shown in the example of FIG. 5. In the example of FIG. 5, the second derivation function 144 derives, as pseudo-feature data, luminance value changes ( ) simulated by inputting the fib concentration into the physical model 152A while increasing the Hb concentration by a predetermined increment AA. In the example of FIG. 5, since the reference data changes from the maximum to the minimum of a luminance change period due to pulsation, the pseudo-feature data is derived from the maximum to the minimum in the same manner, but if the reference data is a range from the minimum to the maximum, the second derivation function 144 derives pseudo-feature data simulated by gradually decreasing the Hb concentration by the predetermined amount AA.

Figure 6:
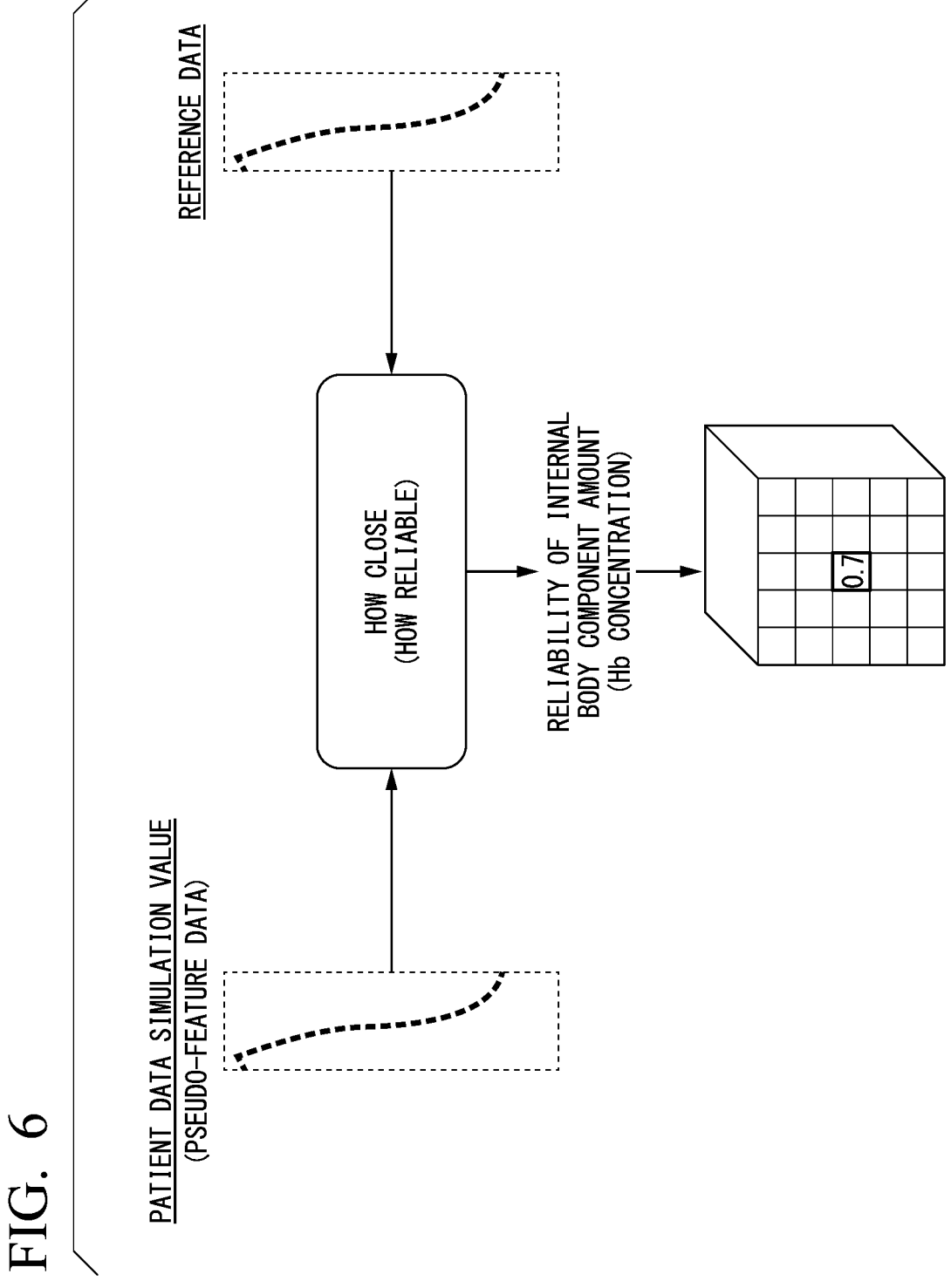
FIG. 6 is a diagram showing a reliability score determination function.

The reliability score determination function 145 determines reliability scores of the internal body component amounts from the reference data derived by the first derivation function 143 and the pseudo-feature data derived by the second derivation function 144. FIG. 6 is a diagram showing the reliability score determination function 145. The reliability score determination function 145 compares the values of the reference data and the pseudo-feature data (patient data simulation value), evaluates how close the two pieces of input data are (how reliable the Hb concentration is), and determine an index value (e.g., a reliability score) that quantifies the similarity of the data. For example, the reliability score determination function 145 may determine a reliability score from the inner product of the two input values. In this case, the reliability score determination function 145 increases the reliability score as the inner product is closer to 1.

The reliability score determination function 145 may determine the reliability score using the reciprocal (1/MAE) of the mean absolute error (MAE) of the two input values or determine the reliability score using the reciprocal (1/MSE) of the mean squared error (MSE) thereof. In this case, the reliability score determination function 145 increases the reliability score as the reciprocal value increases. In addition, the reliability score determination function 145 increases the reliability score as the sums of slopes between two adjacent points become closer in changes in the input values. Further, the reliability score determination function 145 may also use another method of calculating the degree of similarity between the two input values.

The reliability score determination function 145 can obtain reliability scores for the entire image by executing the above-described processing for each pixel of the image included in the patient moving image MV. The reliability score determination function 145 may determine a score only for a predetermined image range that requires a reliability score in the entire image. The image region may be determined on the basis of the imaging position of the patient moving image MV or may be set through the input interface 120 by the user.

Figure 7:
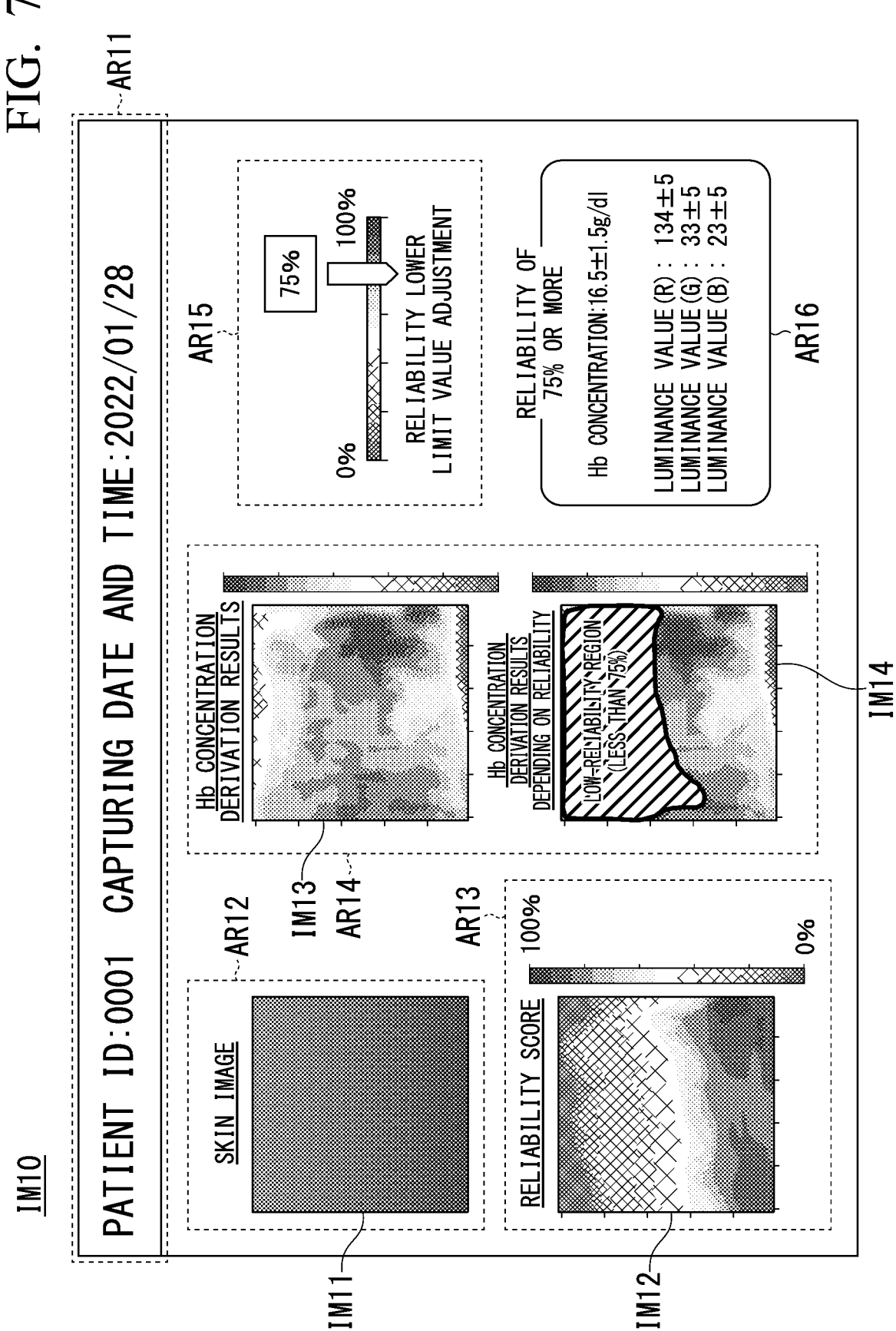
FIG. 7 is a diagram showing an example of a first image generated by an image generation function.

The image generation function 146 generates an image including information on the reliability scores determined by the reliability score determination function 145. FIG. 7 is a diagram showing an example of a first image IM10 generated by the image generation function 146. Display modes such as the details, layout, colors, and design displayed in the image IM10, which will be described below, are not limited to this. The same applies to other images which will be described later.

The image IM10 shown in FIG. 7 includes, for example, a patient information display area AR11, a biometric data display area AR12, a reliability score display area AR13, an internal body component amount display area AR14, a setting input area AR15, and a processing result display area AR16. In the patient information display area AR11, identification information (for example, a patient ID) for identifying a patient whose biometric data has been acquired, and biometric data acquisition date and time (for example, a date and time when a skin image has been captured) are displayed. In the biometric data display area AR12, a target image (a skin image IM11 in the example of FIG. 7) included in the biometric data DB 151, for which reliability scores have been determined, is displayed.

A reliability score distribution image IM12 for the skin image IM11 is displayed in the reliability score display area AR13. Images IM14 and IM15 showing results of derivation of an internal body component amount (for example, Hb concentration) for the skin image IM11 are displayed in the internal body component amount display area AR14. An image for allowing the user to set a lower limit value of the reliability scores is displayed in the setting input area AR15. The example of FIG. 7 shows a slider by which the user can adjust the reliability lower limit value by inputting an operation to the input interface 120 or according to an instruction from the hospital terminal 20. For example, the image generation function 146 displays an image IM14 obtained by masking an area having reliability scores less than the reliability lower limit value in the image IM13 showing Hb concentration derivation results on the basis of the reliability lower limit value set by the user. For example, masking may be superimposing and displaying another image, removing it, or hiding it. This allows the user to ascertain an Hb concentration with a high reliability. In the processing result display area AR16, processing results such as Hb concentrations and luminance values for an image region having reliability values equal to or higher than the reliability lower limit value are displayed.

The display control function 147 causes the image IM10 displayed by the image generation function 146 to be displayed on the display 130 or to be transmitted to the hospital terminal 20 via the network NW. Further, the display control function 147 may store the processing results and the like in the memory 150 or cause information stored in the memory 150 to be displayed on the display 130 or to be transmitted to the hospital terminal 20.

By displaying the first image IM10, for example, the internal body component amounts including the reliability scores can be provided to a doctor or the like. Therefore, the doctor can exclude low-reliability components from the internal body component amounts and make a diagnosis based on highly-reliability data, thereby preventing over-looking of the onset of a disease of a patient and allowing more appropriate diagnoses.

Figure 8:
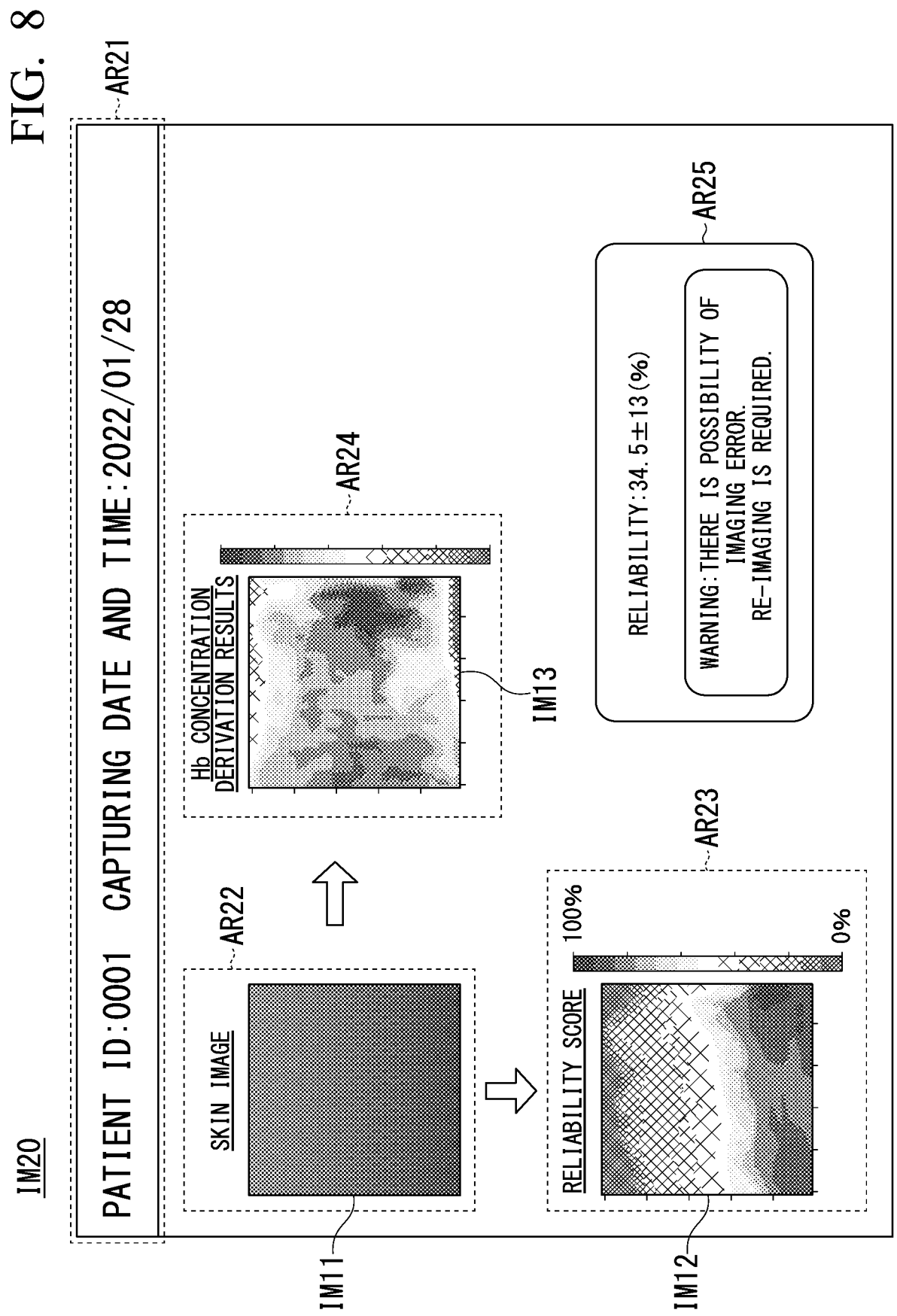
FIG. 8 is a diagram showing an example of a second image generated by the image generation function.

The image generation function 146 may generate other images instead of (or in addition to) the first image IM10. FIG. 8 is a diagram showing an example of a second image IM20 generated by the image generation function 146. The second image 120 includes information for inducing a patient to re-acquire biometric data (re-capture a skin image in the example of FIG. 8).

The second image IM20 shown in FIG. 8 includes, for example, a patient information display area AR21, a bio-metric data display area AR22, a reliability score display area AR23, an internal body component amount display area AR24, and a processing result display area AR25. The patient information display area AR21, the biometric data display area AR22, and the reliability score display area AR23 display the same information as that of the display areas AR11 to AR13 of the first image IM10 described above. An image IM14 showing results of derivation of an internal body component amount (for example, Hb concen-tration) for the skin image IM11 is displayed in the internal body component amount display area AR24. In addition, in the processing result display area AR25, reliability score information (numerical values) for the internal body com-ponent amount to be processed and information regarding the necessity of re-capturing based on processing results are displayed.

For example, if the reliability score of the internal body component amount in the skin image IM11 is less than a threshold value, the image generation function 146 displays information for inducing the patient to re-acquire biometric data (skin image). In the example of FIG. 8, the reliability score (34.5±13 (%)) is less than the threshold value, and thus information indicating that it is necessary to re-acquire biometric data ("Warning: There is a possibility of imaging error. Re-imaging is required.") or the like is displayed in the internal body component amount display area AR24.

When the second image IM20 is generated, the display control function 147 may transmit the second image IM20 to the patient terminal 10 to induce biometric data to be re-acquired and retransmitted in addition to causing the second image IM20 to be displayed on the display 130 or to be transmitted to the hospital terminal 20. Since the patient is induced to re-acquire input data when the reliability score is low by displaying the second image IM20, it is possible to prevent erroneous diagnosis due to information with a low reliability score and overlooking of the onset of a disease (for example, onset of heart failure or varicose veins in the lower extremities).

[Processing Flow]

Figure 9:
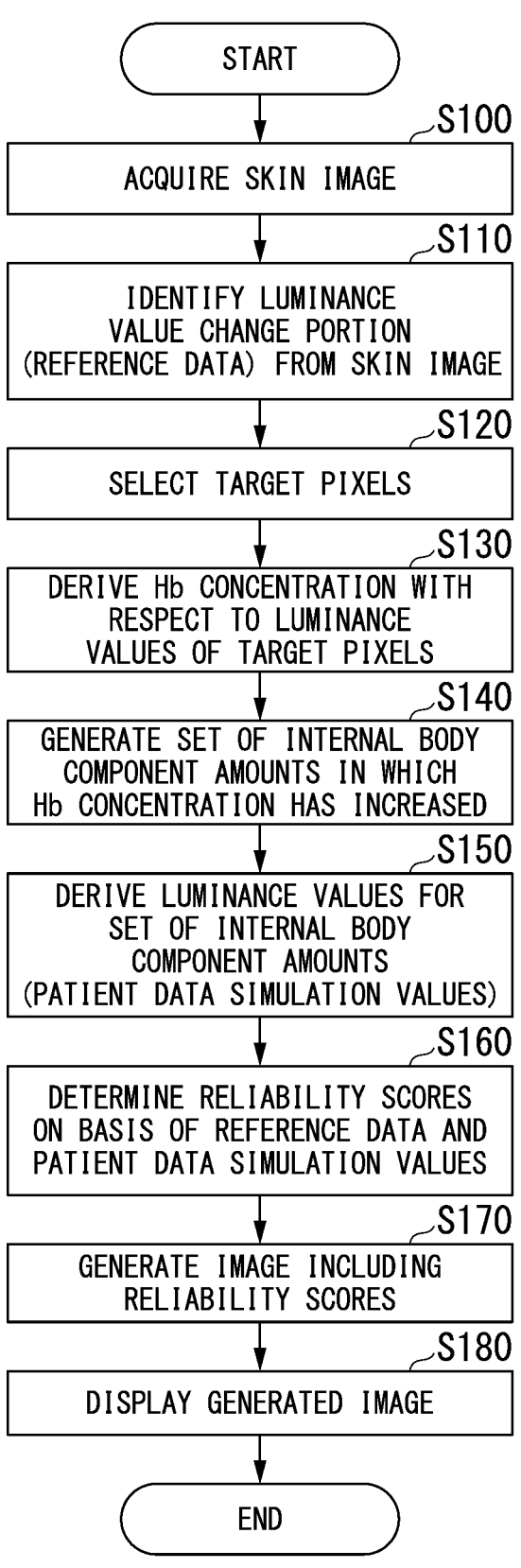
FIG. 9 is a flowchart showing a series of flows of processing executed by processing circuitry.

A processing flow of the processing circuitry 140 in an embodiment will be described below. FIG. 9 is a flowchart showing a series of flows of processing executed by the processing circuitry 140. In the example of FIG. 9, the acquisition function 141 acquires skin images (a moving image including images of a plurality of time phases) in order to acquire internal body component amounts from the biometric data DB 151 (step S100). Next, the reference data identification function 142 identifies a luminance value change portion (reference data) accompanied by Hb con-centration increase due to pulsation from the acquired skin images (step S110).

Next, the first derivation function 143 selects the same target pixels as pixels from which the reference data has been acquired (step S120) and derives a Hb concentration with respect to the luminance value of the selected target pixels (step S130). In addition, the first derivation function 143 also generates a set of internal body component amounts in which the Hb concentration has increased (step S140).

Next, the second derivation function 144 derives lumi-nance values for the set of internal body component amounts to calculate patient data simulation values (pseudo-feature data) (step S150). Next, the reliability score determination function 145 determines reliability scores on the basis of the reference data and the patient data simulation values (step S160). Next, the image generation function 146 generates an image including the reliability scores (step S170). Next, the display control function 147 causes the display 130 to display the generated image (step S180). In step S180, the generated image may be transmitted to an external device (hospital terminal 20) via a network. Accordingly, process-ing of this flowchart ends.

Modified Example

The medical information processing apparatus 100 of the embodiment may use, for example, reliability scores with respect to biometric data calculated by the reliability score determination function 145 at the time of learning a clinical decision support (CDS) model. Hereinafter, this will be described as a modified example of the medical information processing apparatus. Meanwhile, the same names and sym-bols are attached to the same components as those described in the above-described medical information system 1, and detailed descriptions thereof are omitted here.

Figure 10:
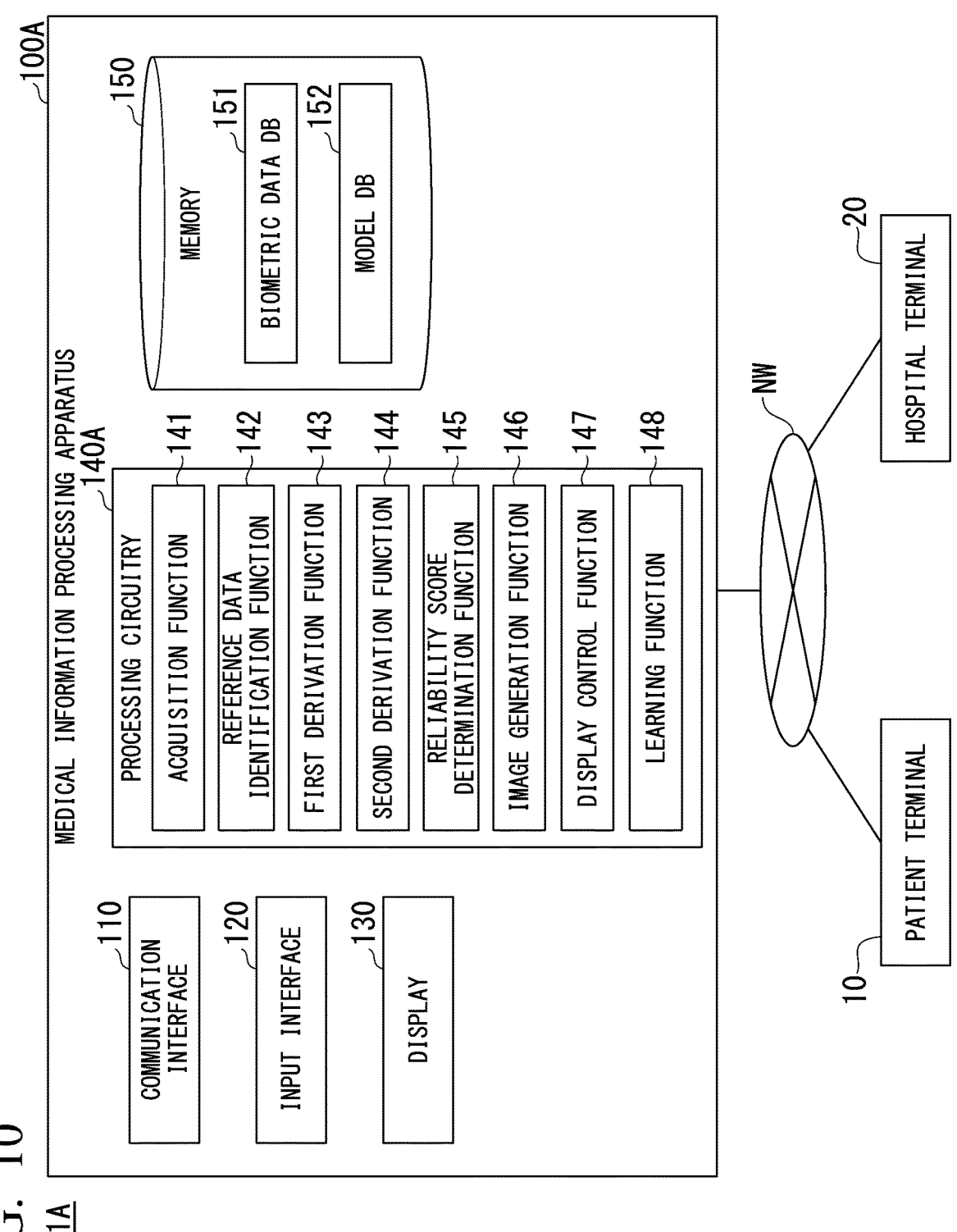
FIG. 10 is a diagram showing an example of a configuration of a medical information system including a medical information processing apparatus of a modified example.

FIG. 10 is a diagram showing an example of a configu-ration of a medical information system 1A including a medical information processing apparatus 100A of a modi-fied example. The medical information system 1 includes, for example, a patient terminal 10, a hospital terminal 20, and the medical information processing apparatus 100A. The patient terminal 10, the hospital terminal 20, and the medical information processing apparatus 100A are con-nected via a network NW such that they can communicate, for example.

The medical information processing apparatus 100A includes, for example, a communication interface 110, an input interface 120, a display 130, processing circuitry 140A, and a memory 150. The processing circuitry 140A includes, for example, an acquisition function 141, a refer-ence data identification function 142, a first derivation function 143, a second derivation function 144, a reliability score determination function 145, an image generation func-tion 146, a display control function 147 and a learning function 148. The processing circuitry 140A differs from the processing circuitry 140 of the medical information process-ing apparatus 100 in that it has the learning function 148. Therefore, the following description will focus on the learn-ing function 148.

The learning function 148 trains a model using biometric data adjusted on the basis of reliability scores determined by the reliability score determination function 145. For example, the learning function 148 trains a CDS model and other models (for example, models stored in the model DB 152) using the reliability scores determined by the reliability score determination function 145. The CDS model is used, for example, in medical sites (for example, the hospital terminal 20), beauty sites, and other sites where image analysis is performed, such as computer aided diagnosis (CAD) systems.

The learning function 148 acquires skin images and performs preprocessing such as smoothing filtering and edge extraction removal thereon. Further, the learning function 148 separates learning data and test data, and selects a region to be used for learning from the separated data on the basis of the reliabilities (reliability scores) determined by the reliability score determination function 145. Specifically, a low-reliability region in which reliability scores of internal body component amounts are less than a threshold value (for example, 75[%]) is masked in the skin images to be trained. Thereafter, the learning function 148 trains the CDS model using unmasked data with reliability scores equal to or greater than the threshold value. For learning, well-known learning methods such as deep learning and other machine learning are used, for example. The learning function 148 may also evaluate the accuracy of learning results.

Figure 11:
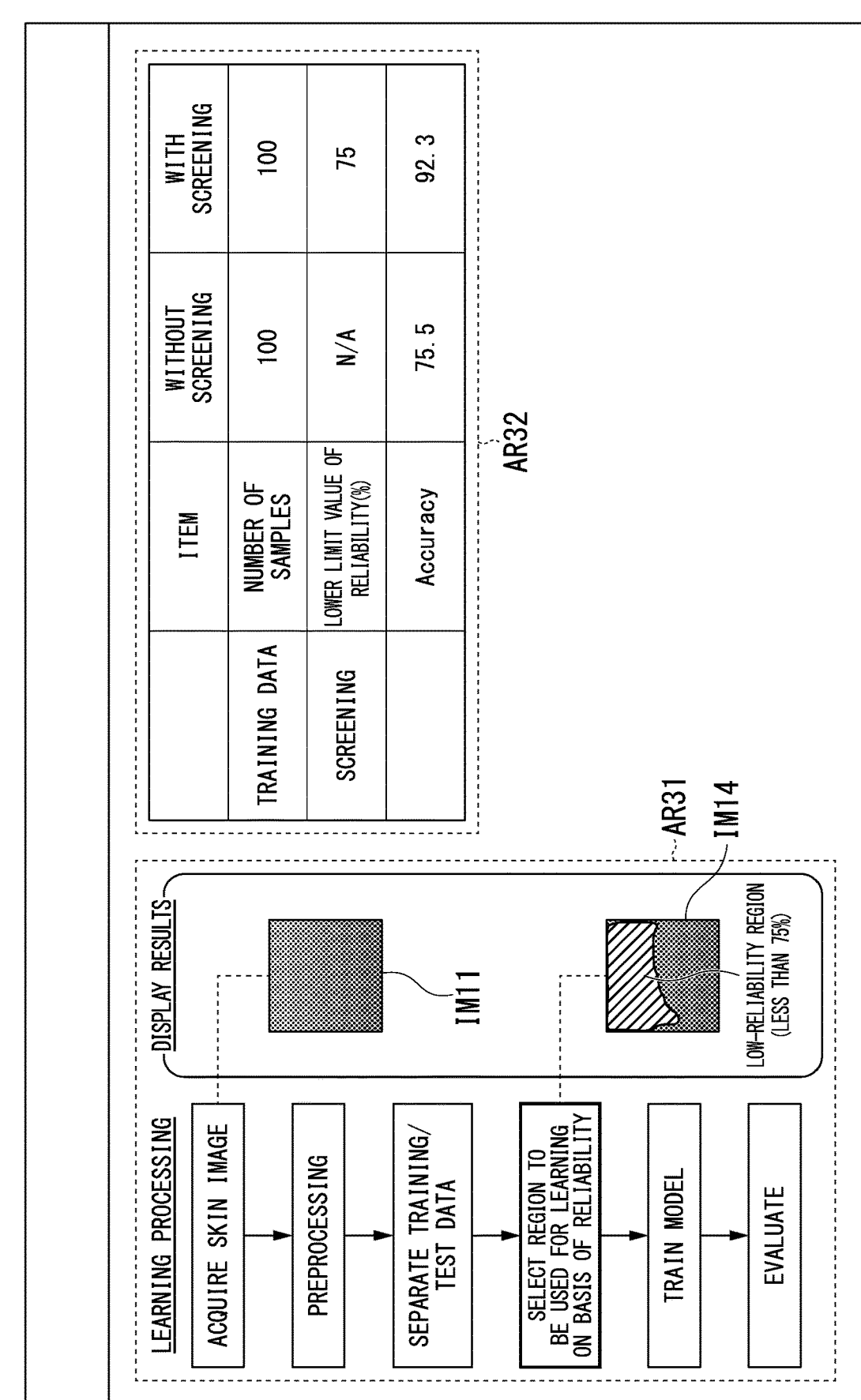
FIG. 11 is a diagram showing an example of a third image generated by the image generation function.

The image generation function 146 generates an image including results processed by the learning function 148. FIG. 11 is a diagram showing an example of a third image IM30 generated by the image generation function 146. In the example of FIG. 11, the image IM30 includes a learning content display area AR31 and a learning result display area AR32. A flow of learning processing executed by the learning function 148 and results of each type of processing are displayed in the learning content display area AR31. In the example of FIG. 11, a skin image IM11 and an image IM14 in which a region with a low reliability score is masked are shown as processing results.

In the learning result display area AR32, for example, the number of samples of training data and evaluation results (accuracy) of the model trained on the basis of presence or absence of screening (mask processing based on reliability scores) are displayed. The display control function 147 displays the generated image on the display 130 or transmits the generated image to an external device via the network NW.

According to the modified example described above, it is possible to use reliability scores to determine whether or not to use them for model training by providing information such as the image IM30 to the user. The medical information processing apparatus 100A may receive a selection as to whether to use data with screening or data without screening for model training from the user via the input interface 120 and perform learning processing corresponding to the received result.

The medical information processing apparatuses 100 and 100A of the embodiments may include at least some functions of the patient terminal 10 and may include at least some functions of the hospital terminal 20. Therefore, the medical information processing apparatuses 100 and 100A may be provided with a function of capturing biometric data of a patient (for example, a patient moving image, and the like), and a doctor or the like may perform diagnosis of the patient while viewing an image displayed on the display 130 of the medical information processing apparatuses 100 and 100A.

In addition, although the Hb concentration is mainly used as a parameter of an internal body component in the above-described embodiments, reliability scores with respect to other internal body component amounts that can be acquired as biometric data (for example, a Mel concentration, a blood sugar level, a venous blood oxygen saturation (SpO2), and an arterial blood oxygen saturation (SvO2) may be determined instead of (or in addition to the Hb concentration). In this case, the medical information processing apparatuses 100 and 100A of the embodiments change parameters of internal body components for which reliability scores will be calculated depending on the details of biometric data acquired by the acquisition function 141 and details of reference data identified by the reference data identification function 142. For example, if the reference data is absorbance detected by a sensor, oxygen saturation in the blood (for example, venous blood oxygen saturation or arterial blood oxygen saturation) is selected as a parameter of an internal body component. In addition, the medical information processing apparatuses 100 and 100A of the embodiments may receive information on a target for which reliability scores will be determined from the user via the input interface 120 and perform processing using the received information on the target.

In addition, although reference data and the like are identified on the assumption that luminance values change due to pulsation in the examples of the above-described embodiments, reference data and the like may be identified on the assumption of luminance value change due to compression of blood vessels using a member such as a cuff (luminance value increases due to decrease in a blood flow rate) instead thereof.

Furthermore, the medical information processing apparatuses 100 and 100A of the embodiments may determine reliability scores on the basis of reference data identified from an image of a single time phase and pseudo-feature data derived from the same image. Further, the medical information processing apparatuses 100 and 100A of the embodiments may determine reliability scores on the basis of a plurality of pieces of reference data and a plurality of pieces of pseudo-feature data. In this case, the reference data identification function 142 identifies reference data for each of a plurality of first feature amounts on the basis of biometric data. Further, the first derivation function 143 derives a plurality of second feature amounts by inputting each of the first feature amounts into a model, and the second derivation function 144 derives a plurality of pieces of pseudo-feature data by inputting the plurality of second feature amounts into the model. Then, the reliability score determination function 145 determines reliability scores on the basis of the plurality of pieces of reference data and the plurality of pieces of pseudo-feature data. In this manner, comparison can be performed under various conditions using a single time phase or a plurality of time phases, and thus more detailed reliability scores can be determined, and an internal body component amount closer to the actual physical condition of a subject can be identified more appropriately.

In the above-described embodiments, the acquisition function 141 is an example of an "acquisition unit," the reference data identification function 142 is an example of a "reference data identification unit," the first derivation function 143 is an example of a "first derivation unit," the second derivation function 144 is an example of a "second derivation unit," the reliability score determination function 145 is an example of a "reliability score determination unit," the image generation function 146 is an example of an "image generation unit," the display control function 147 is an example of a "display control unit," and the learning function 148 is an example of a "learning unit."

According to at least one embodiment described above, the medical information processing apparatus of the embodiment can identify an internal body component amount closer to the actual physical condition of a subject more appropriately by including an acquisition unit that acquires biometric data regarding the subject, a reference data identification unit that that identifies reference data regarding a first feature amount on the basis of the biometric data, a first derivation unit that acquires a second feature amount by inputting the first feature amount included in the biometric data into a model capable of mutually converting the first feature amount and the second feature amount, a second derivation unit that derives pseudo-feature data regarding the first feature amount simulated by inputting the second feature amount into the model, and a reliability score determination unit that determines reliability scores regarding the biometric data on the basis of the reference data and the pseudo-feature data.

Specifically, according to the embodiment, it is possible to exclude internal body component amounts with low reliability and prevent overlooking of the onset of a disease of a patient, and the like in diagnosis of a doctor by deriving features based on change in internal body component amounts as reference data, deriving pseudo-feature data simulated with respect to the internal body component amounts using a model, and quantifying the reliability of the internal body component amounts from the data, resulting in appropriate diagnosis.

Further, according to the embodiment, information for inducing re-acquisition of data can be provided with respect to biometric data with low reliability scores to obtain appropriate biometric data, and internal body component amounts close to the actual physical condition of a subject can be identified more appropriately. Therefore, it is possible to prevent overlooking of the onset of a disease of a patient, and the like.

Furthermore, according to the present embodiment, it is possible to obtain a model with higher accuracy by using only information with a high reliability score for model training.

The embodiment described above can be represented as follows.

A medical information processing apparatus including:
a memory storing a program; and
a processor,
wherein the processor is configured to, by executing the program:
acquire biometric data regarding a subject;
identify reference data regarding a first feature amount on the basis of the biometric data;
acquire a second feature amount by inputting the first feature amount included in the biometric data into a model capable of mutually converting the first feature amount and the second feature amount;
derive pseudo-feature data regarding the first feature amount simulated by inputting the second feature amount into the model; and
determine reliability scores with respect to the biometric data on the basis of the reference data and the pseudo-feature data.

Although several embodiments have been described, these embodiments are presented as examples and are not intended to limit the scope of the invention. These embodiments can be implemented in various other forms, and various omissions, substitutions, and modifications can be made without departing from the spirit of the invention. These embodiments and modifications thereof are included in the scope and spirit of the invention, as well as the scope of the invention described in the claims and equivalents thereof.

What is claimed is:

1. A medical information processing apparatus, comprising:
processing circuitry configured to:
acquire biometric data regarding a subject, including a captured image of skin of the subject;
identify reference data showing characteristics that reflect changes in parameters of internal body components based on a first feature amount included in the biometric data;
acquire a second feature amount by inputting the first feature amount into a model stored in a memory configured to mutually convert between the first feature amount and the second feature amount containing parameters of the internal body components;
derive pseudo-feature data regarding the first feature amount simulated by changing at least some of the parameters of the internal body components included in the second feature amount to enable comparison with the reference data;
determine reliability scores with respect to the parameters of the internal body components based on a degree of similarity between the reference data and the pseudo-feature data; and
generate and display an output image including information of the determined reliability scores.

2. The medical information processing apparatus according to claim 1, wherein the biometric data acquired by the processing circuitry is biometric data of a single time phase or a plurality of time phases.

3. The medical information processing apparatus according to claim 1, wherein the first feature amount is a feature amount derived from the biometric data, and the second feature amount is a feature amount derived from the first feature amount.

4. The medical information processing apparatus according to claim 1, wherein the processing circuitry is further configured to:
identify a plurality of pieces of reference data for each of a plurality of first feature amounts based on the biometric data;
derive a plurality of second feature amounts by inputting the first feature amounts into the model;
derive a plurality of pieces of pseudo-feature data by inputting the plurality of second feature amounts into the model; and
determine the reliability scores based on the plurality of pieces of reference data and the plurality of pieces of pseudo-feature data.

5. The medical information processing apparatus according to claim 1, wherein the biometric data includes an image, and the processing circuitry is further configured to determine a respective reliability score for each pixel included in the image or in a predetermined image range.

6. The medical information processing apparatus according to claim 1, wherein the processing circuitry is further configured to generate an image including information on the reliability scores.

7. The medical information processing apparatus according to claim 6, wherein the processing circuitry is further configured to generate the output image by masking a region where the reliability scores are less than a threshold value in an area of an image acquired as the biometric data of the subject.

8. The medical information processing apparatus according to claim 6, wherein the processing circuitry is further configured to generate an image for inducing re-acquisition of the biometric data, in response to determining that the reliability scores are less than the threshold value.

9. The medical information processing apparatus according to claim 1, wherein the processing circuitry is further configured to train the model using the biometric data adjusted based on the reliability scores.

10. The medical information processing apparatus of claim 1, further comprising sensors configured to measure sensor data being a hemoglobin concentration, a melanin concentration, a blood oxygen saturation level, or a blood sugar level of the subject, the sensor data being acquired by the processing circuitry as part of the biometric data.

11. A medical information processing method, using a computer, the method comprising:

acquiring biometric data regarding a subject, including a captured image of skin of the subject;

identifying reference data showing characteristics that reflect changes in parameters of internal body components based on a first feature amount included in the biometric data;

acquiring a second feature amount by inputting the first feature amount into a model stored in a memory, the model being configured to mutually convert between the first feature amount and the second feature amount containing parameters of the internal body components;

deriving pseudo-feature data regarding the first feature amount simulated by changing at least some of the parameters of the internal body components included in the second feature amount to enable comparison with the reference data:

determining reliability scores with respect to the parameters of the internal body components based on a degree of similarity between the reference data and the pseudo-feature data; and generating and displaying an image including information of the determined reliability scores.

12. A non-transitory computer-readable recording medium storing a program causing a computer to:

acquire biometric data regarding a subject, including a captured image of skin of the subject;

identify reference data showing characteristics that reflect changes in parameters of internal body components based on a first feature amount included in the biometric data;

acquire a second feature amount by inputting the first feature amount into a model stored in a memory, the model being configured to mutually convert between the first feature amount and the second feature amount containing parameters of the internal body components;

derive pseudo-feature data regarding the first feature amount simulated by changing at least some of the parameters of the internal body components included in the second feature amount to enable comparison with the reference data;

determine reliability scores with respect to the parameters of the internal body components based on a degree of similarity between the reference data and the pseudo-feature data; and generate and display an image including information of the determined reliability scores.

\* \* \* \* \*